(12) United States Patent
Jackson et al.

(10) Patent No.: US 7,350,428 B2
(45) Date of Patent: Apr. 1, 2008

(54) APPARATUS AND PROCESS FOR COLLECTION OF GAS AND VAPOR SAMPLES

(75) Inventors: Dennis G. Jackson, Augusta, GA (US); Kurt D. Peterson, Aiken, SC (US); Brian D. Riha, Augusta, GA (US)

(73) Assignee: Westinghouse Savannah River Company LLC, Aiken, SC (US)

( * ) Notice: Subject to any disclaimer, the term of this patent is extended or adjusted under 35 U.S.C. 154(b) by 382 days.

(21) Appl. No.: 11/143,028

(22) Filed: Jun. 2, 2005

(65) Prior Publication Data
US 2006/0272431 A1    Dec. 7, 2006

(51) Int. Cl.
*G01N 1/00* (2006.01)
(52) U.S. Cl. .................................. 73/864.63
(58) Field of Classification Search ............... 73/864, 73/864.31, 864.33, 864.34, 864.51, 864.52, 73/864.61, 864.63, 23.41, 23.42
See application file for complete search history.

(56) References Cited

U.S. PATENT DOCUMENTS

| | | | | |
|---|---|---|---|---|
| 2,374,227 A | * | 4/1945 | Metcalf | .................... 73/864.52 |
| 4,219,986 A | | 9/1980 | Osterhaus | |
| 4,539,852 A | | 9/1985 | Feld | |
| 4,552,278 A | * | 11/1985 | Romanauskas | ............. 215/277 |
| 5,579,626 A | | 12/1996 | Thomas | |
| 5,662,230 A | | 9/1997 | Finneran | |
| 5,772,057 A | | 6/1998 | Finneran | |
| 5,857,579 A | | 1/1999 | Finneran | |
| 5,925,029 A | | 7/1999 | Jansen et al. | |
| 6,076,330 A | | 6/2000 | Thomas et al. | |
| 6,199,436 B1 | | 3/2001 | Morel et al. | |
| 6,213,994 B1 | | 4/2001 | Jansen et al. | |
| 6,250,046 B1 | | 6/2001 | VandeGeijn | |
| 6,367,301 B1 | | 4/2002 | Bassani | |
| 6,453,641 B1 | | 9/2002 | Puckett | |
| 6,477,919 B1 | | 11/2002 | Thomas et al. | |
| 2003/0051890 A1 | * | 3/2003 | Marshall | ..................... 173/206 |

\* cited by examiner

*Primary Examiner*—Robert Raevis
(74) *Attorney, Agent, or Firm*—J. Bennett Mullinax, LLC

(57) ABSTRACT

A gas sampling apparatus and process is provided in which a standard crimping tool is modified by an attached collar. The collar permits operation of the crimping tool while also facilitating the introduction of a supply of gas to be introduced into a storage vial. The introduced gas supply is used to purge ambient air from a collection chamber and an interior of the sample vial. Upon completion of the purging operation, the vial is sealed using the crimping tool.

12 Claims, 5 Drawing Sheets

APPARATUS AND PROCESS FOR COLLECTION OF GAS AND VAPOR SAMPLES

STATEMENT AS TO RIGHTS TO INVENTIONS MADE UNDER FEDERALLY SPONSORED RESEARCH AND DEVELOPMENT

This invention was made with Government support under Contract No. DE-AC0996-SR18500 awarded by the United States Department of Energy. The Government has certain rights in the invention.

FIELD OF THE INVENTION

This invention is directed towards an apparatus and process for use in the collection of gas and vapor samples which may then be shipped to a separate location for analysis by gas chromatography or other analytical techniques.

BACKGROUND OF THE INVENTION

There are a variety of techniques and products available for the collection of gas and vapor samples. In particular, gas samples containing organic constituents such as volatile organic compounds (VOCs) are collected from a location such as a contaminated field site or an industrial waste stream. The analytical equipment needed to analyze the organic constituents within the sample typically requires the commercial transport of a sealed collection container to a laboratory.

There are a variety of collection techniques and products known for carrying out such sampling. For instance, it is known to use absorbent traps, inert bags such as Tedlar® bags, and vacuum canisters such as a Summa® canister to collect and transport gas and vapor samples. It is also known in the art to use sealed glass vials having an elastomeric septum defined within the vial closure. Syringes can be used to pierce the septum and introduce a gaseous sample into the interior of the vial upon which the needle is carefully removed to avoid tearing of the septum.

While the above techniques are useful, the apparatuses and/or protocols used to collect samples can be expensive and require numerous manual steps which are time consuming. To the extent the insertion of needles within a septum is used to insert a sample into a vial, there is always a risk of damage to the septum which may compromise the integrity of the sample. In addition, techniques which rely upon larger apparatuses such as the Summa® type canisters are costly to transport and process.

Accordingly, there remains room for improvement and variation within the art.

SUMMARY OF THE INVENTION

It is one aspect of at least one of the present embodiments to provide for a gas sampling apparatus and process which may use disposable commercially available, off-the-shelf glass vials of a standard size for collecting a sample and which may then be sealed with an airtight closure.

It is a further aspect of at least one of the present embodiments of the invention to provide for a gas collection apparatus which allows a standard vial crimping tool to be used in association with a gas sample filling process.

It is yet a further aspect of at least one embodiment of the present invention to provide for a sample collection collar which is adapted for operative engagement with a standard glass vial crimping tool. The collar provides for the delivery of a gas or vapor sample to an associated glass vial while the collar is attached to a crimping tool. The crimping tool can then be used to apply a sealed cap to the glass vial.

It is yet an additional aspect of at least one of the present embodiments of the invention to provide for a process of collecting a gas sample comprising the steps of supplying a glass vial crimping tool; attaching a collar to the crimping tool, the collar adapted for receiving a gas sample and delivering the gas sample to an interior space defined by the collar; inserting a glass vial to a first position within the collection collar; introducing a gas stream into the collar housing and into the vial for a time sufficient to purge ambient air from the vial; positioning the vial containing a sample of the gas into a second position within the collar; applying a sealed closure to the vial; and, removing the vial from the collar, the vial containing therein a known volume of the gaseous sample.

It is yet an additional aspect of at least one of the present embodiments of invention to provide for a sample collection collar which can be used with a standard vial crimping tool. The sample collection collar may be used with a manual vial crimping tool or may be incorporated into an automated apparatus and process in which an automated actuator, manipulator, and vial load/unload mechanisms may be used.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Figure 1:
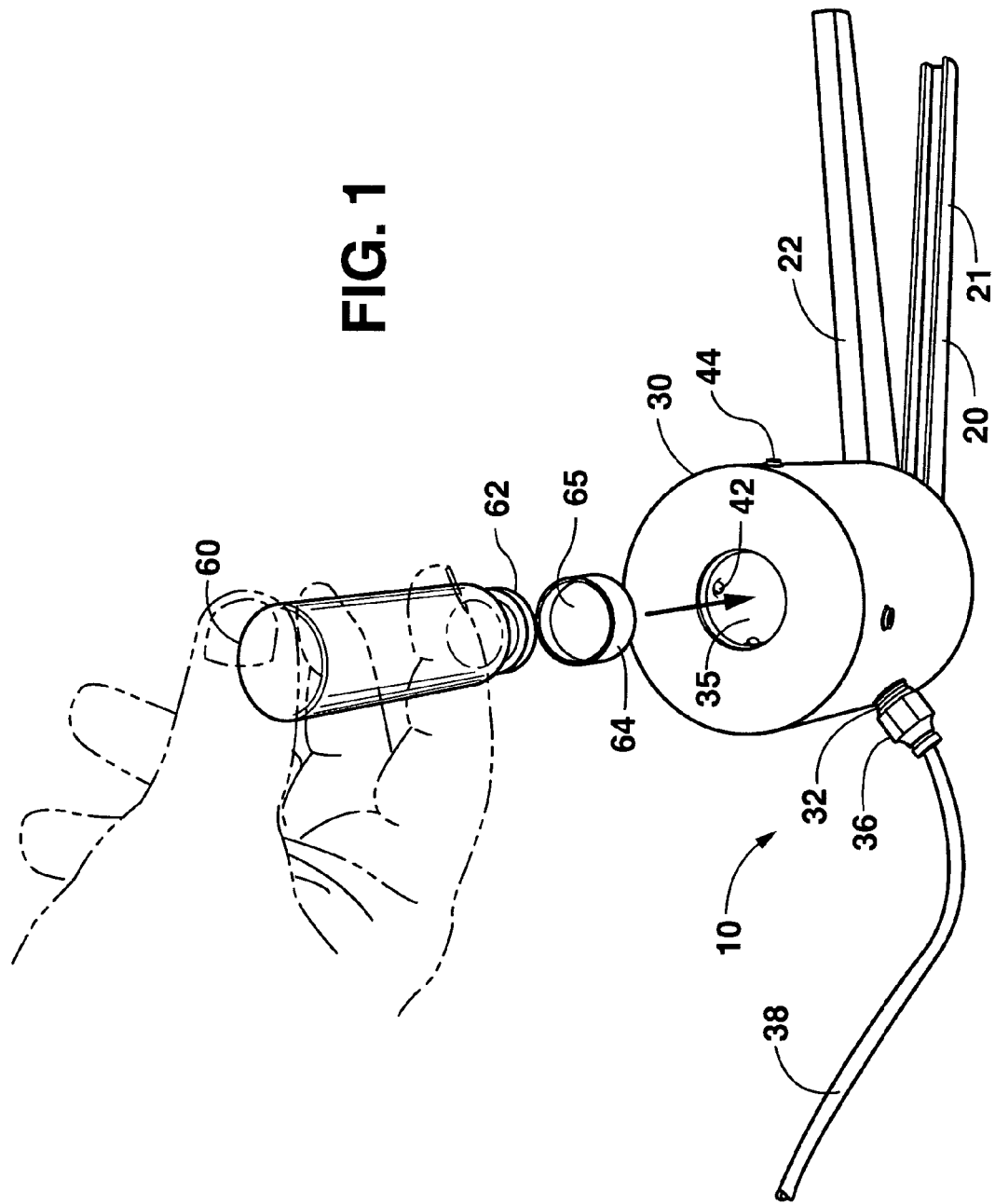
FIG. 1 is an exploded view of a sampling apparatus illustrating the position of a sample vial and a closure for insertion into the collection and sealing assembly.
Figure 2:
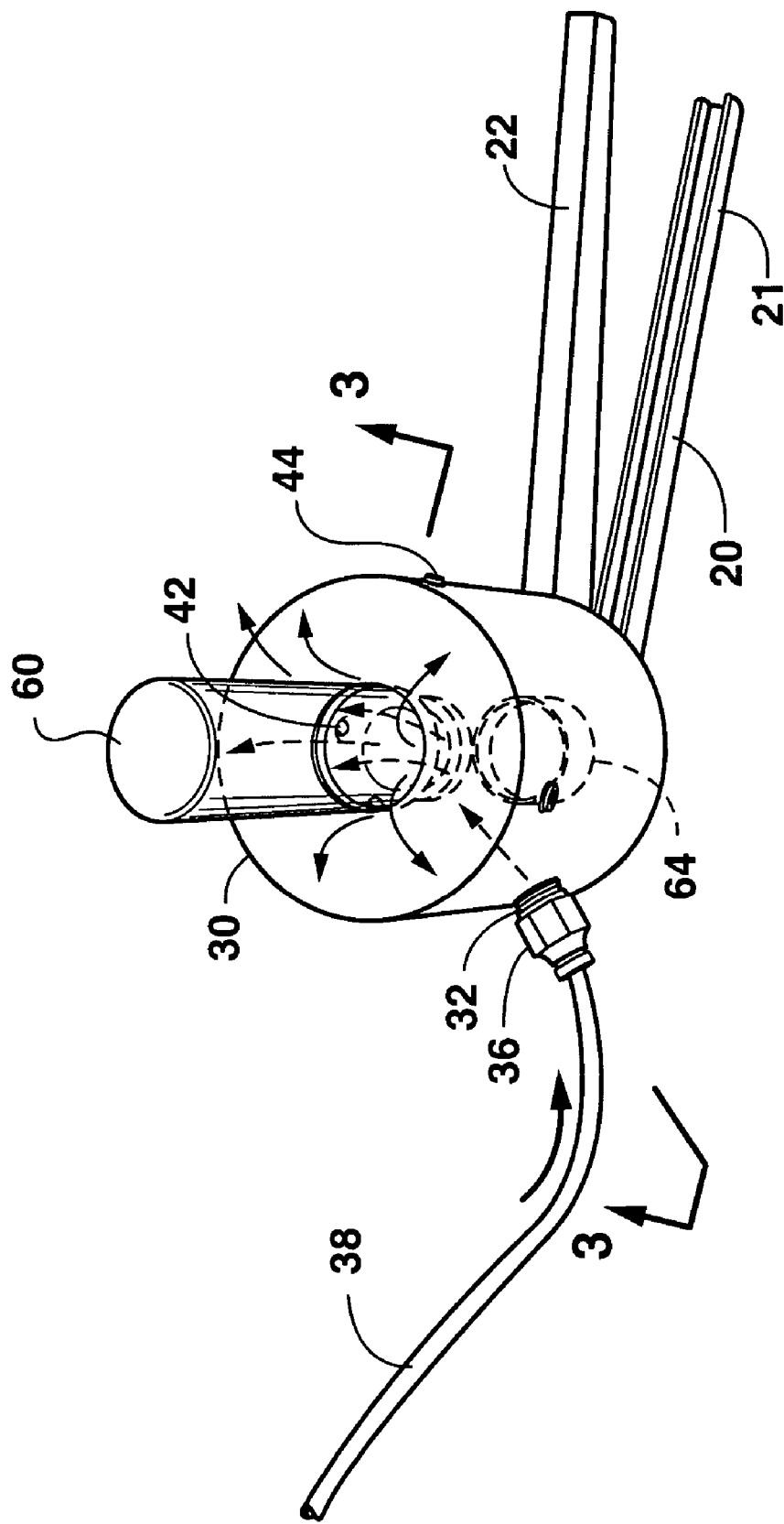
FIG. 2 is a perspective view in partial phantom showing the insertion of a collection vial within the collection apparatus.

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

An embodiment of the present invention is herein illustrated in reference to FIGS. 1 through 5B. As best seen in reference to FIG. 3, a standard crimping tool 20 having handles 21 and 22 has multiple jaws 24 which are designed to receive a vial 60 having an opening 62. A closure 64 may be crimped into position around opening 62 so as to provide a fluid tight seal to vial 60. Crimping tools 20 are conventional within the art and are provided from a variety of manufacturers. One such manufacturer is National Scientific Company which provides a standard 20 mm crimping tool having part number C4020-100 (Duluth, Ga.). Suitable crimping tools for modification according to the present invention include the crimping tools set forth in U.S. Pat. No. 5,579,626 assigned to Chromatography Research Supplies, Inc., U.S. Pat. No. 6,453,641 assigned to National Scientific Company, and U.S. Pat. No. 6,076,330 of Thomas et al, the specifications and disclosures of which are incorporated by reference.

The crimping tool is designed to work with metal caps and septums which are sized for the crimping tool and appropriate vial. The vial size and materials for the vial, vial cap, and vial cap septum are conventional within the art and may be selected for compatibility with the gas being sampled as well as subsequent analysis requirements. In one of the present embodiments, nominal 20 ml head space vials such as those provided by Agilent Technologies, Product #5188-2759 (Palo Alto, Calif.) or Wheaton Science Products, Product #225280 (Millville, N.J.) may be found useful along with an appropriately selected cap and septum.

The present apparatus uses a collar 30 which is adapted to replace a threaded skirt which is part of a conventional crimping tool 20. Upon removal of the skirt and insertion of the threaded collar 30 onto the crimping tool 20 the collar 30 thereafter provides a chamber in which a gas or vapor sample may be supplied to the interior of the collar which also facilitates the crimping of a cap onto an introduced vial.

Figure 3:
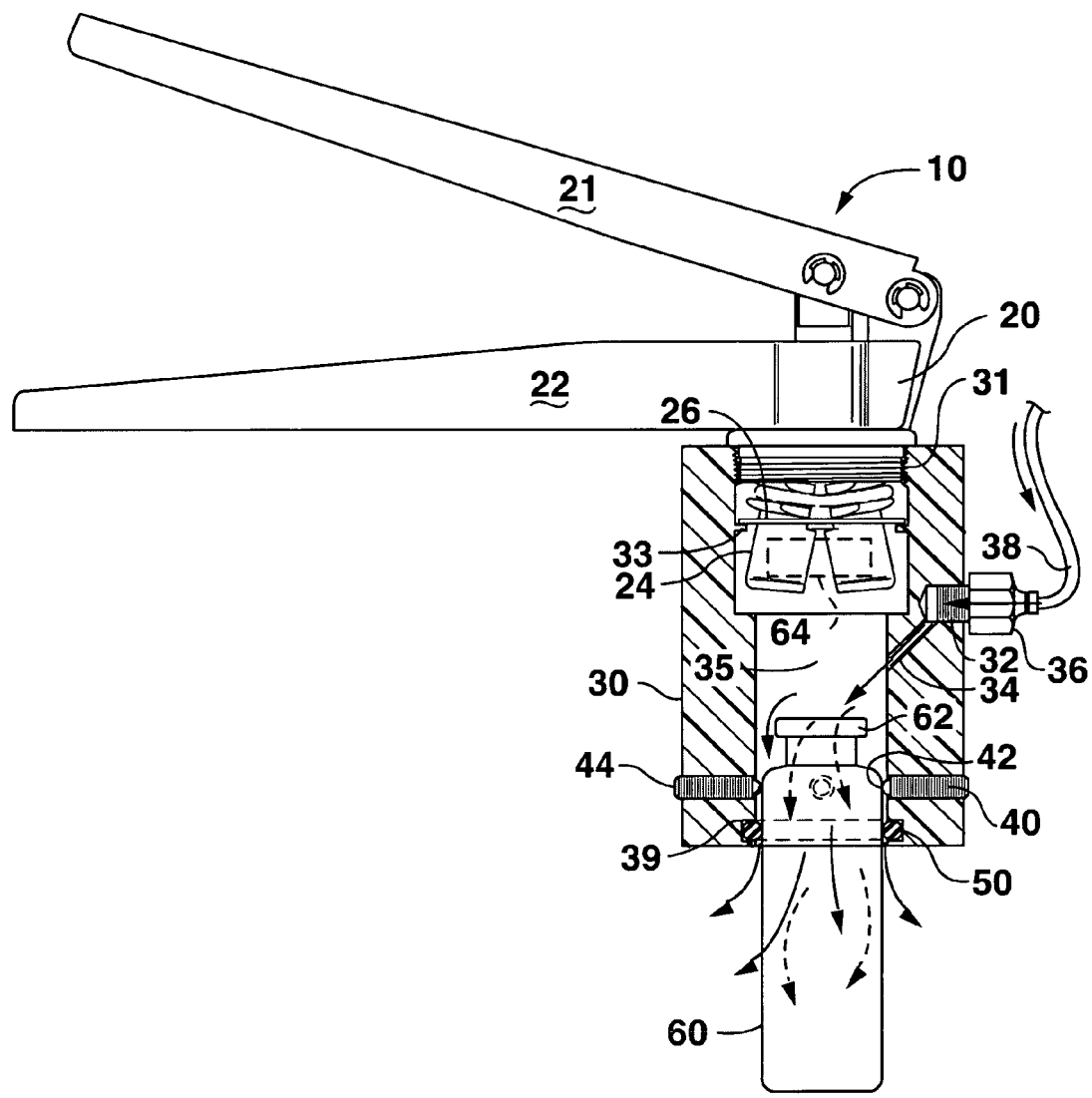
FIG. 3 is a cross-sectional view as seen along the lines 3-3 of FIG. 2.
Figure 4:
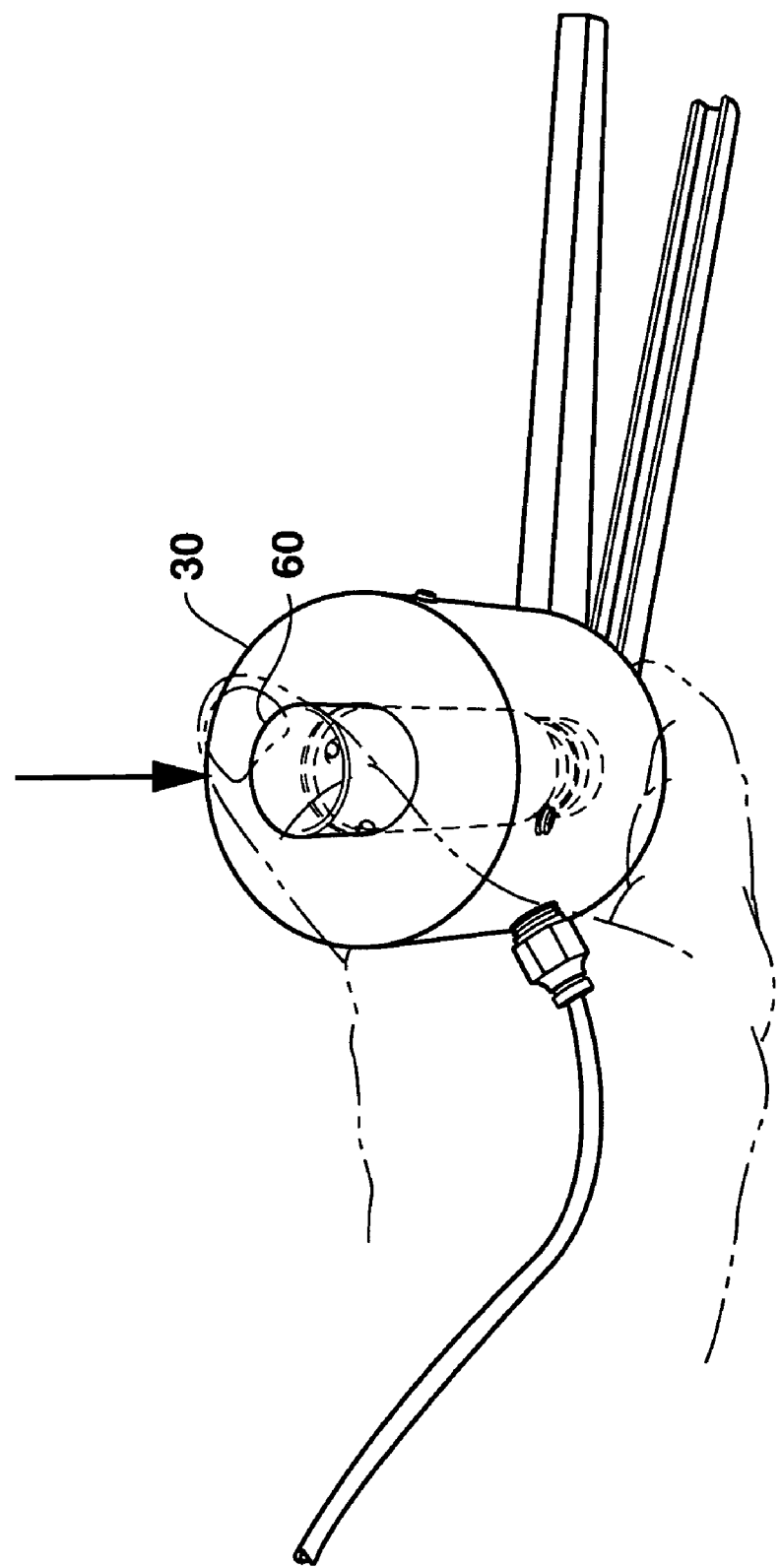
FIG. 4 is a perspective view in partial phantom illustrating the positioning of the vial in preparation for a sealing step.
Figures 5A, 5B:
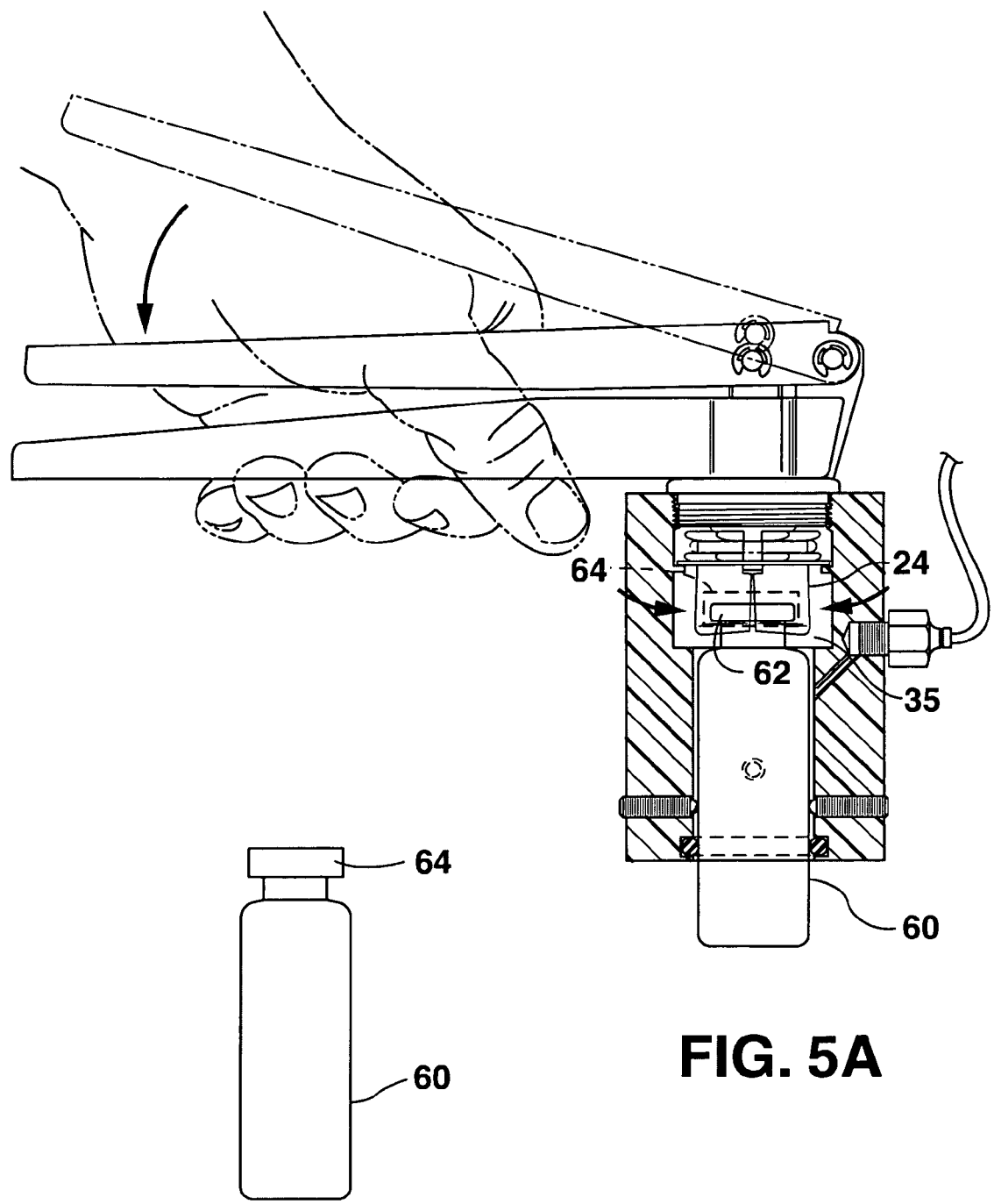
FIG. 5A is a sectional view similar to FIG. 3 showing a cap being applied to the vial.
FIG. 5B illustrates a sealed vial once removed from the collection apparatus.

As seen in FIG. 3, an upper portion of collar 30 defines a threaded region 31 which will engage a standard crimping tool. Within a chamber 35 defined within an interior of collar 30, there is a small ledge 33 defined which is designed to engage a ring 26 which extends around an exterior of crimping jaws 24. When crimping tool 20 is engaged by pressing handle 21 toward handle 22, ring 26 is pushed against ledge 33 thereby providing the jaw closing force as is typically used to bring about jaw closure of a conventional crimping tool.

As further seen in reference to FIG. 3, the chamber 35 has an upper portion having a greater diameter than a lower portion of chamber 35. The upper portion of chamber 35 is sized so as to receive jaws 24 in an open configuration. The lower portion of chamber 35 can be of a different diameter which is preferably sized to accommodate the shape of an inserted vial 60. In the embodiment illustrated in FIG. 3, vial 60 may have a cylindrical shape and the corresponding diameter of a lower portion of chamber 35 may be smaller than the upper portion of chamber 35.

In reference to FIG. 1, collar 30 has been secured to crimping tool 20. An unsealed cap 64 having an elastomeric septum 65 is positioned within an opening to the chamber 35 of collar 30. As further seen in reference to FIGS. 2 through 4, vial 60 may then be inserted into chamber 35 and used to insert the closure 64 into a crimping position within the crimping jaws 24. As best seen in reference to FIGS. 2 and 4, prior to a crimping operation, the glass vial 60 is partially withdrawn from chamber 35, placing the vial 60 in a filling position. As seen in the illustrated manual embodiment, gravity may be used to hold the cap closure 64 in the crimping position within the multiple jaws 24 until the crimping tool is actuated.

As seen in FIG. 3, an indexing station 40 is provided within collar 30 and which comprises a positional pin 42 which is responsive to a spring within a housing 44. A plurality of index stations 40 are arranged within collar 30 so as to hold an upper edge of vial 60 in a stationary position during a sample filling operation. In association with the index stations 40, there is an "O" ring 50 positioned within a groove 39 defined by an inner wall of chamber 35 which additionally engages an exterior wall of vial 60. "O" ring 50 provides an additional securement force for retaining the vial within the chamber 35. "O" ring 50 also provides for reduced fluid flow between the edges of vial 60 and the contact region with "O" ring 50.

As further seen in FIG. 3, collar 30 is in communication with a gas supply line 38. While a variety of various connections between supply line 38 and collar 30 are possible, one such combination is illustrated as a threaded inlet 32 which extends part way into collar 30 and further extends outwardly from an exterior of collar 30. A threaded coupling 36 is used to connect a supply line 38 to connector 36 in a manner that provides for a sealed delivery of a gas sample from supply line 38 into the threaded inlet 32. Collar 30 further defines a bore 34 which connects inlet 32 to chamber 35. As seen in FIG. 3, the bore 34 may be provided at an approximately 45 degree angle so as to direct a gas sample toward a bottom of chamber 35 to provide turbulence and mixing within vial 60 as seen by the directional arrows. As illustrated by the arrows, the introduced gas supply is directed generally toward the opening 62 of vial 60. The gas sample is directed to the interior of the inserted vial 60 which generates a purging effect with respect to the vial. In addition, a portion of the air/sample volume within the chamber 35 is forced along the outer edge walls of vial 60 and through openings present within the jaw assembly 24 and crimping tool 20. It is important that the inter-engagement of vial 60 within collar 30 does not provide for a completely fluid tight seal so as to prevent pressure from the introduced gas sample from ejecting the vial 60 from the collar 30.

The volume and velocity of the gas sample which is introduced can be easily regulated. It is desirable to have a sufficient volume and velocity of gas so as to create a purging effect of ambient air within the interior of vial 60 along with purging of any ambient air present within a chamber 35 of collar 30. In accordance with this invention, it has been found that an interval of between 30 seconds to 60 seconds is sufficient to purge ambient air from vial 60 and chamber 35 and allow for a representative gas sample to be introduced into the interior of vial 60.

Following the introduction of the gas sample into vial 60, the vial is inserted further within collar 30 so as to engage the closure 64 which is snap crimped onto vial opening 62 by the operation of crimping tool 20. Subsequently, when the vial having cap 64 sealed thereto is removed from collar 30, the contents of the vial 60 provide for a sealed gas sample which can be easily transported to a location for analysis of the vial contents.

It has been found that the integrity of the closure 64 to vial 60 provides for a sufficiently air tight seal such that the sample integrity is maintained for at least a 7 day interval which is more than adequate for typical transportation and analysis. It is noted that any number of gas or vapor analytical techniques may be used in that the contents of the vial can be easily withdrawn using a needle collection device which will pierce the septum 65 in order to withdraw the contents of vial 60.

Collar 30 can be provided from a variety of materials. Since samples to be collected through collar 30 may include reactive or corrosive constituents, it is preferred that collar 30 be constructed of an inert material such as a plastic, nylon, urethane, high density polyethylene, passivated steel, or similar material which is chemically inert to the gas being collected. Such materials may be easily machined so as to provide chamber 35, threads 31, bore 34, openings to house the plurality of pins 42 and housings 44 which make up the respective indexing stations 40 and groove 39. Similarly, "O" ring 50 is preferably of a chemically inert elastomer.

The collar 30 and associated crimping tool 20 which make up the collection apparatus 10 is easily transported and may be used both in field and laboratory conditions. Further, the collar 30 may be easily installed or removed. In addition, the original crimping tool 20 is easily restored to its original operational design. In addition, the collar 30 allows the apparatus 10 to be used for conventional operations which involve no flow of gas through the collar.

The collar 30 may also be adapted for use with an automated crimping operation and process. For instance, automated crimping stations and capping apparatuses are known in the art as set forth in U.S. Pat. No. 4,219,986 assigned to Perry Industries, Inc., and U.S. Pat. No. 6,250,046 assigned to VandeGeijn, and which are incorporated herein by reference. Both the above referenced disclosures teach an automated process for applying caps to containers. In each instance, the capping station could be conducted in associated with an apparatus such as collar 30 as set forth within this disclosure so as to provide for a method of purging ambient air from the vial's interior while introducing a representative sample of a gas supply which is to be collected within the vial. As known in the art, the various steps of positioning an individual vial from a supply of vials to a capping station is known. Likewise, the steps of manipulating the vial to a loading station and a crimping station and the actuation of a crimping tool are well known. In the present instance, the loading station and crimping station occurs in a single location and within a housing such as the housing provided by collar 30. In this manner, an automated gas sample collection process and apparatus can be provided so as to provide for unintended operation of any desired interval or frequency of collecting samples from a gas supply. The modification of an automated capping apparatus and the process in view of the teachings set forth herein are well within the skill level of one having ordinary skill in the art.

Accordingly, while the illustrated embodiments set forth herein show a manually operated embodiment, such illustration is not limiting to the broader aspects of the invention as set forth within the accompanying claims. The scope of the accompanying claims are consistent with both a manually operated crimping tool as well as an automated crimping process.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention which is set forth in the following claims. In addition, it should be understood that aspects of the various embodiments may be interchanged, both in whole, or in part. Therefore, the spirit and scope of the appended claims should not be limited to the description of the preferred versions contained therein.

That which is claimed:

1. An apparatus for introducing a gas sample into a container comprising:
    a crimping tool comprising a handle, a plurality of jaw members, and an actuator mechanism;
    a collar operatively engaging said crimping tool so as to enclose said plurality of jaw members when said actuator mechanism of said handle is engaged;
    a chamber defined by an interior of said collar, said chamber having an opening at one end and opposite said crimping tool;
    an inlet having a first end and a second end, said inlet defined within a sidewall of said collar and being in communication at said first end with said chamber and said second end providing communication with an exterior of said collar;
    wherein a sample of a gas is introduced through said inlet into an interior of said chamber, said chamber further adapted for placement of a vial within said chamber for receiving a portion of said gas within said vial.

2. The apparatus according to claim 1 wherein said inlet is positioned at about a 45 degree angle relative to a horizontal reference plane defined by an upper edge of said vial.

3. The apparatus according to claim 1 wherein a plurality of spring biased tension pins are in communication with said chamber.

4. The apparatus according to claim 1 wherein an interior wall of said chamber defines a groove therein, said groove adapted for receiving an "O" ring.

5. The apparatus according to claim 1 wherein said chamber defines a circumferential ledge extending along an inner wall of said chamber.

6. The apparatus according to claim 1 wherein a lower portion of said chamber is adapted for receiving a cylindrical vial therein.

7. A process for collecting a gas sample within a vial comprising:
    providing a crimping tool comprising, a plurality of jaw members, and an actuator mechanism, said crimping tool further comprising a collar operatively engaging said crimping tool so as to close said plurality of jaw members when said actuator mechanism is engaged;
    positioning a collection vial within a chamber defined by an interior of said collar;
    introducing a sample gas supply to said chamber, said sample gas supply purging both said chamber and an interior of said sample vial of ambient air; and, sealing said sample vial using said crimping tool once a representative gas sample has been established in an interior of said vial.

8. The process according to claim 7 wherein said step of positioning a collection vial within a chamber is a manual step.

9. The process according to claim 7 wherein said step of positioning a collection vial within a chamber is an automated step.

10. The process according to claim 7 wherein following said purging step, said vial is then placed in a different location within the chamber prior to the sealing step.

11. An apparatus for introducing a gas sample into a container comprising:

a crimping tool comprising a plurality of jaw members, said jaw members closing in response to an actuator mechanism;

a collar operatively engaging said crimping tool, said collar defining a bore extending therethrough, said bore having a first opening adapted for receiving a portion of said crimping tool within a first end of said collar, said bore having a second opening in communication with an exterior of said collar;

an inlet having a first end and a second end, said inlet defined within a sidewall of said collar and being in communication at said first end with said bore and said second end providing communication with an exterior of said collar;

wherein a sample of gas is introduced through said inlet into said bore, said second bore opening further adapted for placement of a vial within said chamber for receiving a portion of said gas within said vial.

12. The apparatus according to claim 11 wherein when said vial and a cap are placed within said jaw members, said crimping tool engages said cap and applies said cap to said vial.

* * * * *